(12) United States Patent
Wendland et al.

(10) Patent No.: US 11,202,861 B2
(45) Date of Patent: Dec. 21, 2021

(54) INJECTION DEVICE

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 380 days.

(21) Appl. No.: 15/778,293

(22) PCT Filed: Nov. 21, 2016

(86) PCT No.: PCT/EP2016/078256
§ 371 (c)(1),
(2) Date: May 23, 2018

(87) PCT Pub. No.: WO2017/089267
PCT Pub. Date: Jun. 1, 2017

(65) Prior Publication Data
US 2018/0353693 A1  Dec. 13, 2018

(30) Foreign Application Priority Data

Nov. 27, 2015  (EP) .................................... 15196687

(51) Int. Cl.
*A61M 5/20* (2006.01)
*A61M 5/32* (2006.01)

(52) U.S. Cl.
CPC ........ *A61M 5/2033* (2013.01); *A61M 5/3202* (2013.01); *A61M 5/3204* (2013.01);
(Continued)

(58) Field of Classification Search
CPC .................... A61M 5/178; A61M 5/20; A61M 2005/2006; A61M 5/32; A61M 5/321;
(Continued)

(56) References Cited

U.S. PATENT DOCUMENTS

| 2007/0073224 A1* | 3/2007 | Dries ................. A61M 5/3243 604/110 |
| 2012/0186075 A1* | 7/2012 | Edginton ............ A61M 5/2033 29/700 |
| 2016/0184531 A1* | 6/2016 | Schiller ............... A61M 5/3204 604/506 |

FOREIGN PATENT DOCUMENTS

| WO | WO 2008/086004 | 7/2008 |
| WO | WO 2011/001161 | 1/2011 |

(Continued)

OTHER PUBLICATIONS

PCT International Preliminary Report on Patentability in International Appln. No. PCT/EP2016/078256, dated May 29, 2018, 7 pages.

(Continued)

*Primary Examiner* — Jason E Flick
(74) *Attorney, Agent, or Firm* — Fish & Richardson P.C.

(57) ABSTRACT

The present disclosure relates to an injection device. The injection device comprises a body for holding a syringe that has a needle at one end and a cap that is removably attached to the body. The cap has a needle shield to cover said needle. The injection device further comprises a gear assembly comprising a first rotary gear and a first linear gear to engage with the first rotary gear. The gear assembly is configured such that rotation of the first rotary gear drives the first linear gear to urge the needle shield away from the body. An actuator is provided that is configured to rotate the first rotary gear.

21 Claims, 5 Drawing Sheets

(52) U.S. Cl.
CPC ....... *A61M 5/326* (2013.01); *A61M 2005/206* (2013.01); *A61M 2005/2013* (2013.01)

(58) Field of Classification Search
CPC .............. A61M 5/3243; A61M 5/2033; A61M 2005/2013; A61M 2005/206; A61M 5/3202; A61M 5/3204; A61M 5/326
See application file for complete search history.

(56) References Cited

FOREIGN PATENT DOCUMENTS

| WO | WO 2014/154498 | 10/2014 |
|---|---|---|
| WO | WO 2015/020823 | 2/2015 |

OTHER PUBLICATIONS

PCT International Search Report and Written Opinion in International Appln. No. PCT/EP2016/078256, dated Feb. 13, 2017, 11 pages.

\* cited by examiner

INJECTION DEVICE

CROSS REFERENCE TO RELATED APPLICATIONS

This application is a U.S. national stage application under 35 USC § 371 of International Application No. PCT/EP2016/078256, filed on Nov. 21, 2016, which claims priority to European Application No. 15196687.6, filed on Nov. 27, 2015, the entire contents of which are incorporated herein by reference.

TECHNICAL FIELD

The present disclosure relates to an injection device.

BACKGROUND

Injection devices, such as auto-injectors, are known in the art for dispensing a medicament to the injection site of a patient. Such injection devices typically comprise a body and a cap. A needle syringe is located in the body. The cap is removably attached to the body to shield the needle of the needle syringe. To dispense the medicament, the cap is first removed from the body to expose the needle. The needle is then inserted into the body of the patient at the injection site to dispense the medicament.

It is important that the cap is held onto the body with sufficient force to ensure that the cap is not accidentally removed from the body during transport and storage of the injection device. This ensures that the needle is kept sterile and also prevents the sharp needle from causing injury. However, the force required to hold the cap and body together can make it difficult for the patient to intentionally remove the cap from the body prior to injection, particularly if the patient is elderly or infirm.

SUMMARY

An injection device is provided that comprises a body for holding a syringe that has a needle at one end; a cap that is removably attached to the body and has a needle shield to cover said needle; a gear assembly comprising a first rotary gear and a first linear gear to engage with the first rotary gear, configured such that rotation of the first rotary gear drives the first linear gear to urge the needle shield away from the body; and, an actuator configured to rotate the first rotary gear.

The gear assembly and actuator may be configured to reduce the force that must be exerted by the patient to urge the needle shield away from the body. Therefore, separation of the needle shield from the body can be made easier. In addition, the gear assembly and actuator may allow for a controlled separation of the needle shield from the body.

The first linear gear may be fixed relative to the needle shield. Thus, rotation of the first rotary gear causes the first linear gear to be urged away from the body such that the needle shield is urged away from the body. In one such embodiment, the first linear gear is formed in a peripheral surface of the needle shield. Therefore, the first linear gear can be formed from the same component as the needle shield such that the manufacturing complexity and/or cost of the injection device is reduced. Alternatively, the first linear gear may be formed in the body or outer cap.

In one embodiment, the cap further comprises an outer cap, and the needle shield is slidable relative to the outer cap such that the needle shield slides relative to the outer cap when the first rotary gear is rotated. Therefore, the injection device may be arranged such that the cap is retained on the body after the needle shield has been urged away from the body. The user may then remove the cap from the body. The cap may be retained on the body by friction and/or by a clip.

In one embodiment, the first rotary gear is rotatably coupled to the body. Thus, the needle shield is urged away from the body when the first rotary gear is rotated. In an alternative embodiment, the first rotary gear is rotatably coupled to the cap. Thus, the needle shield is moved relative to the cap and is urged away from the body when the first rotary gear is rotated.

The actuator may comprise a lever arm that has an end fixed relative to the first rotary gear.

In one embodiment, the actuator is slidable relative to the body to rotate the first rotary gear. The sliding movement of the actuator relative to the body may make the actuator easier to operate. The actuator may comprise a second linear gear that is configured to cause the first rotary gear to rotate when the actuator is slid relative to the body. The injection device may comprise a second rotary gear that couples the second linear gear to the first rotary gear.

In one embodiment, the gear assembly is configured to have a gear ratio such that a force exerted on the actuator translates into a larger force being exerted on the needle shield. This facilitates separation of the needle shield from the body.

The injection device may comprise a plurality of gear assemblies. This may allow for a more even exertion of force on the needle shield to urge the needle shield away from the body.

In one embodiment, the injection device comprises a syringe having a needle at one end and being received in the body, and the needle shield is in frictional engagement with the syringe when the cap is attached to the body. The friction may help to retain the needle shield on the syringe. The syringe may contain a medicament.

In one embodiment, each linear gear is a rack gear and each rotary gear is a pinion gear. In an alternative embodiment, each linear gear is a friction gear and each rotary gear is a friction gear. In yet another embodiment, each linear gear is a rack gear and each rotary gear is a ratchet gear. The ratchet gear may comprise a plurality of flexible elements. The gear assembly may be configured such that rotation of the ratchet gear in a first rotational direction drives the first linear gear to urge the needle shield away from the body, and rotation of the ratchet gear in a second rotational direction, opposite the first rotational direction, does not drive the first linear gear. In one embodiment, the actuator is movable relative to the body from a first position to a second position to urge the first rotary gear to rotate in the first rotational direction. The actuator may be biased into the first position by a biasing member.

In one embodiment, the lever arm extends substantially parallel to the longitudinal axis of the body in a first position.

In one embodiment, the injection device is an auto-injector.

A method is also provided for removing a cap from a body of an injection device, wherein the body holds a syringe that has a needle at one end and wherein the cap is removably attached to the body and has a needle shield to cover the needle, comprising: moving an actuator relative to the cap or body to rotate a first rotary gear, wherein the injection device comprises a first linear gear that is coupled to the first rotary gear such that said rotation of the first rotary gear drives the first linear gear to urge the needle shield away from the body.

The injection device may comprise one or more of the features of the injection device described hereinbefore.

These and other aspects of the invention will be apparent from and elucidated with reference to the embodiments described hereinafter.

BRIEF DESCRIPTION OF THE DRAWINGS

Embodiments will now be described, by way of example only, with reference to the accompanying drawings, in which.

DETAILED DESCRIPTION

Figure 1A:
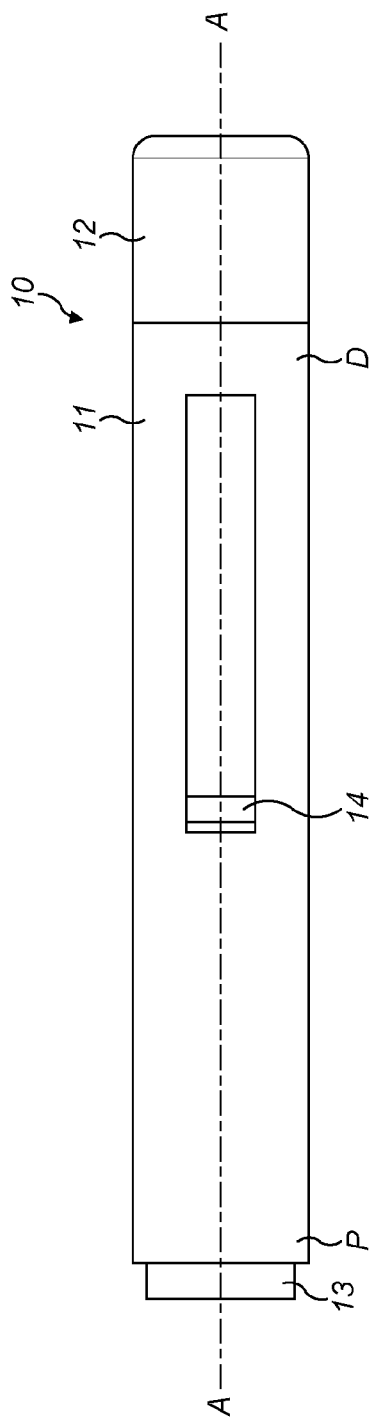
FIG. 1A is a schematic side view of an auto-injector with a cap attached to a body of the auto-injector.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
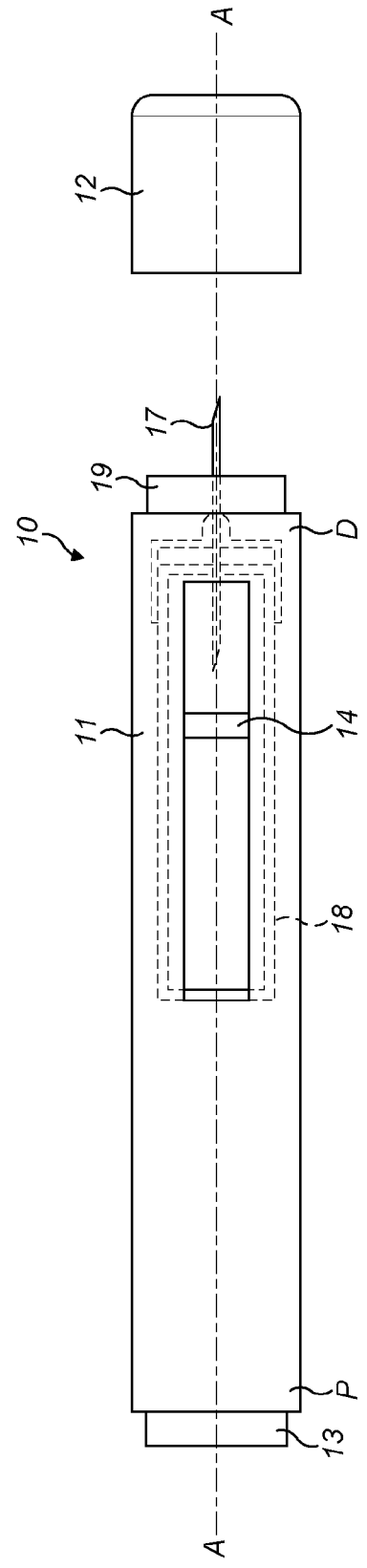
FIG. 1B is a schematic side view of the auto-injector of FIG. 1A, with the cap removed from the body.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated," whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2:
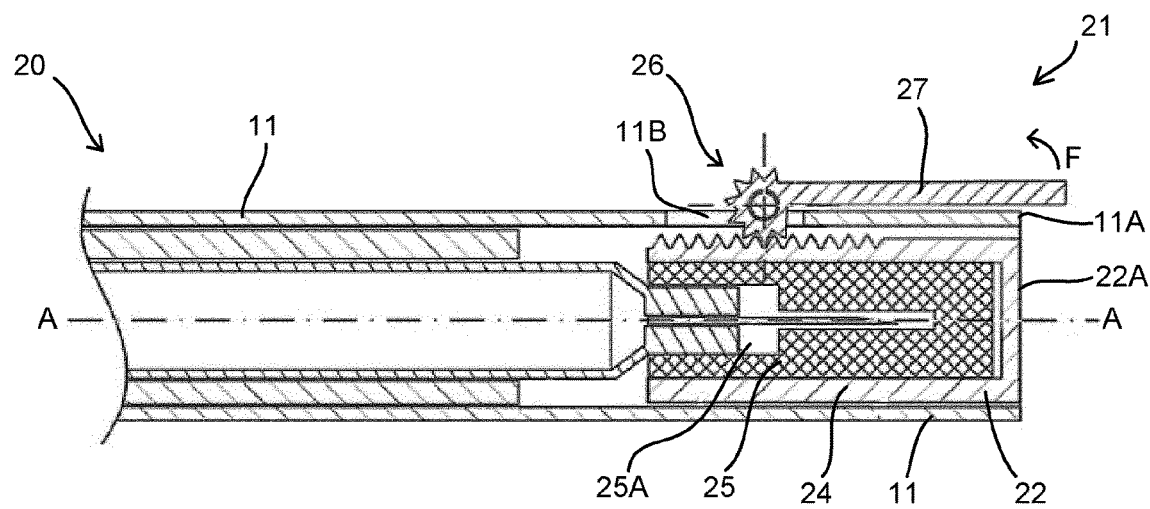
FIG. 2 is a schematic cross-sectional side view of an auto-injector according to a first embodiment, wherein a cap is attached to a body of the auto-injector.
Figure 3:
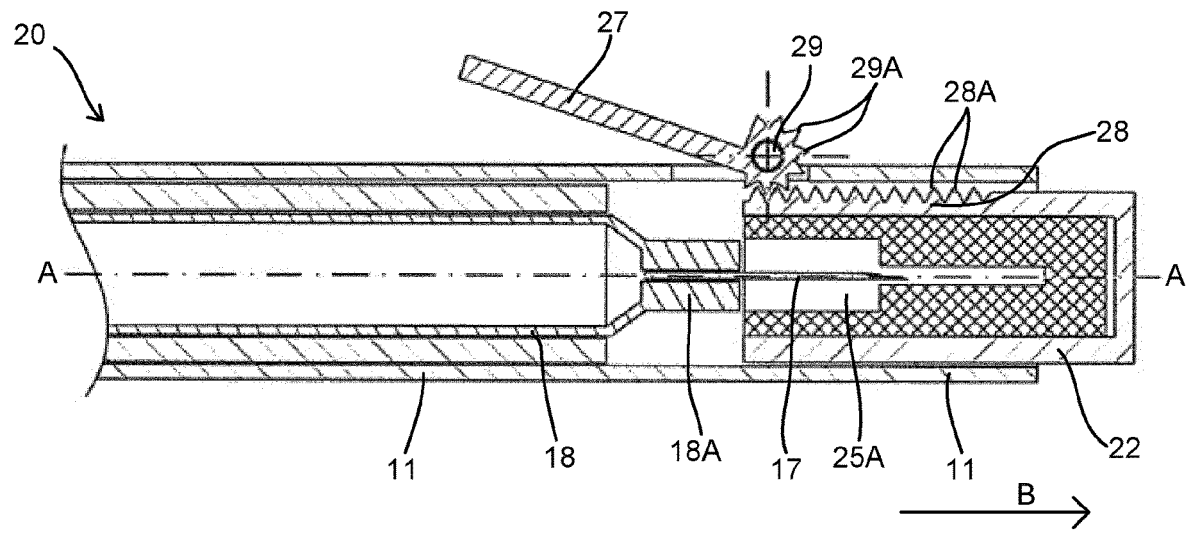
FIG. 3 is a schematic cross-sectional side view of the auto-injector of FIG. 2, wherein the cap is partially removed from the body.

Referring now to FIGS. 2 and 3, part of an injection device 20 according to a first embodiments shown. The injection device 20 is in the form of an auto-injector 20 that has similar features to the auto-injector 10 described above in relation to FIGS. 1A and 1B, with like features retaining the same reference numerals. A difference is that the cap 12 of the auto-injector 10 described above is omitted and is replaced with an alternative cap 21.

The cap 21 of the auto-injector 20 of the first embodiment comprises a needle shield 22 that has a housing 24 and an inner sheath 25. The inner sheath 25 is fixedly secured in the housing 24. The inner sheath 25 comprises a cylindrical recess 25A. The recess 25A is configured to receive an end portion 18A of the syringe 18 such that the needle 17 is shielded by the inner sheath 25. The friction between the inner sheath 25 and the end portion 18A of the syringe 18 is sufficient to hold the needle shield 22 in place covering the needle 17.

The cap 21 further comprises a gear assembly 26 and an actuator 27. The gear assembly 26 comprises a linear gear 28, in the form of a rack gear 28, and a rotary gear 29, in the form of a pinion gear 29. The rack gear 28 is in the form of a plurality of teeth 28A formed in a peripheral surface of the housing 24 of the needle shield 22 such that the rack gear 28 is fixed relative to the inner sheath 25.

The pinion gear 29 is rotatably mounted to the body 11 such that the teeth 29A of the pinion gear 29 engage with the teeth 28A of the rack gear 28. The pinion gear 29 is rotatably mounted in an aperture 11B in the peripheral wall of the body 11. The gear assembly 26 is configured such that rotation of the pinion gear 29 urges the rack gear 28 to move linearly in the direction of the central axis A-A of the auto-injector 20.

The actuator 27 is in the form of a lever arm 27. The lever arm 27 is fixed at one end to the pinion gear 29 such that the patient can exert a force on the lever arm 27 to pivot the lever arm 27 about the rotational axis of the pinion gear 29 such that the pinion gear 29 is urged to rotate. The rotation of the pinion gear 29 causes the rack gear 28 to move linearly relative to the pinion gear 29 in the direction of the central axis A-A of the auto-injector 20 such that the needle shield 22 is moved relative to the body 11.

When the lever arm 27 is in a first position (shown in FIG. 2), the lever arm 27 extends substantially parallel to the central axis A-A of the auto-injector 20. Furthermore, the needle shield 22 is received in the body 11 and the distal end 22A of the needle shield 22 is axially aligned with the open distal end 11A of the body 11 when the lever arm 27 in the first position.

The cap 21 is initially attached to the body 11 such that the end portion 18A of the syringe 18 is completely received in the recess 25A of the inner sheath 25 (as shown in FIG. 2) and the lever arm 27 is in the first position. Thus, the needle 17 is covered by the needle shield 22 to keep the needle 17 sterile and to prevent the needle 17 from causing injury to the patient.

To inject medicament, the cap 21 is first removed from the body 11. Removal of the cap 21 from the body 11 is achieved by the patient exerting a force on the lever arm 27 relative to the body 11 (in the direction of arrow 'F' in FIG. 2) to urge the lever arm 27 to pivot about the rotational axis of the pinion gear 29. This causes the pinion gear 29 to be urged to rotate such that the rack gear 28 is urged to move linearly relative to the body 11 (in the direction of arrow 'B' in FIG. 3) such that the needle shield 22 is urged axially away from the body 11.

The needle 17 is fixed relative to the body 11. Therefore, as the needle shield 22 is urged away from the body 11 due to the patient moving the lever arm 27 away from the first position, the needle shield 22 moves axially away from the needle 17 such that the inner sheath 25 is removed from the end portion 18A of the syringe 18. The patient continues to move the lever arm 27 away from the first position until it is rotated about the rotational axis of the pinion gear 29 to a second position (shown in FIG. 3) wherein the end portion 18A of the syringe 18 is no longer received in the recess 25A of the inner sheath 25. Once the end portion 18A of the syringe 18 has been fully removed from the recess 25A in the inner sheath 25, the friction between the cap 21 and the body 11 is reduced such that the cap 21 can easily be removed from the body 11 simply by pulling the housing 24 of the needle shield 22 away from the body 11.

With the cap 21 removed from the body 11, the open distal end 11A of the body 11 is pressed up against an injection site of the patient. The dispense button (not shown) is then pressed to cause the dispense mechanism (not shown) to move the needle 17 towards the injection site and to dispense medicament to the injection site. In an alternative embodiment (not shown), the dispense mechanism is configured such that movement of the needle towards the injection site and/or the dispensing of the medicament occurs automatically when the open distal end of the body is pressed against the injection site. In one alternative embodiment (not shown), the needle projects from the open distal end of the body when the needle shield is removed, and the needle and syringe remain stationary relative to the body.

The gear assembly 26 and lever arm 27 are configured to reduce the force that must be exerted by the patient to remove the needle shield 22 from the end portion 18A of the syringe 18. This is because the lever arm 27 exerts leverage on the pinion gear 29 such that a force exerted by the patient on the end of the lever arm 27 that is remote to the pinion gear 29 is translated into a greater force acting on the needle shield 22 to urge the needle shield 22 away from the end portion 18A of the syringe 18. Therefore, removal of the cap 21 from the body 11 is made easier. In addition, the gear assembly 26 and lever arm 27 allow for a smooth and controlled separation of the needle shield 22 from the end portion 18A of the syringe 18.

In the above described embodiment, the cap 21 comprises a needle shield 22 having a housing 24 and an inner sheath 25. In another embodiment (not shown), the cap further comprises an outer cap. The needle shield may be disposed inside the outer cap. The needle shield may be secured to the outer cap or may be integrally formed therewith. In one embodiment, the outer cap is integrally formed with the housing and inner sheath of the needle shield. The rack gear may, for example, be formed in a surface of the needle shield or outer cap.

Although in the above described embodiment the pinion gear 29 is rotatably connected to the body 11, in alternative embodiments (not shown) the pinion gear 29 is rotatably connected to the cap 21. In one such alternative embodiment (not shown), the cap further comprises an outer cap that is removably attached to the body. The needle shield is slidably received in the outer cap and the pinion gear is rotatably coupled to the outer cap. Therefore, pivotal movement of the lever arm about the rotational axis of the pinion gear results in a force being exerted on the rack gear that urges the needle shield relative to the outer cap such that the needle shield moves axially away from the body.

Although in the above described embodiment the rack gear 28 is in the form of a plurality of teeth 28A formed in a peripheral surface of the housing 24 of the needle shield 22, in an alternative embodiment (not shown) the rack gear is in the form of a plurality of teeth formed in a peripheral surface of the body and the pinion gear is rotatably mounted to the cap.

In one alternative embodiment (not shown), the housing of the needle shield is omitted and instead the needle shield comprises a sheath with a plurality of teeth formed in a peripheral surface thereof that form the rack gear. Thus, the rack gear is fixed relative to the sheath.

In the above described embodiment, the needle 17 is arranged to move towards the injection site after the cap 21 has been removed from the body 11 and the dispense button has been pressed. However, it should be recognized that in an alternative embodiment (not shown) the needle 17 remains stationary. In one such embodiment, the needle 17 is arranged such that it projects out of the open distal end 11A of the body 11. Thus, once the needle shield 22 has been removed from the needle 17 the user may press the open distal end 11A of the body 11 against the injection site such that the needle 17 is urged into the injection site to dispense medicament thereto. Therefore, providing the needle 17 projects a sufficient amount out of the open distal end 11A of the body 11, it is not necessary for the needle 17 to be moved towards the injection site by a dispensing mechanism.

In the above described embodiment the lever arm 27 extends substantially parallel to the central axis A-A of the auto-injector 20. Therefore, the auto-injector 20 is compact when the lever arm 27 is in the first position and so is easy to store and transport. However, is shall be recognized that in other embodiments (not shown) the lever arm may be configured to extend at an angle to the central axis off the auto-injector. In one such embodiment, the lever arm extends at an acute angle to the central axis of the auto-injector when the lever arm is in the first position such that the lever arm extends towards the peripheral end of the auto-injector. Therefore, the lever arm and body may be squeezed towards each other to move the lever arm away from the first position to urge the needle shield away from the body. This squeezing movement may be easier for a patient to perform, particularly if the patient is elderly or infirm, and facilitates one-handed operation of the auto-injector.

In the above described embodiment, the distal end 22A of the needle shield 22 is axially aligned with the open distal end 11A of the body 11 when the lever arm 27 in the first position. However, in an alternative embodiment (not shown), the distal end 22A of the needle shield 22 may extend axially past the open distal end 11A of the body 11 when the lever arm 27 is in the first position. Alternatively, the open distal end 11A of the body 11 may extend axially past the distal end 22A of the needle shield 22 when the lever arm 27 is in the first position.

Figure 4:
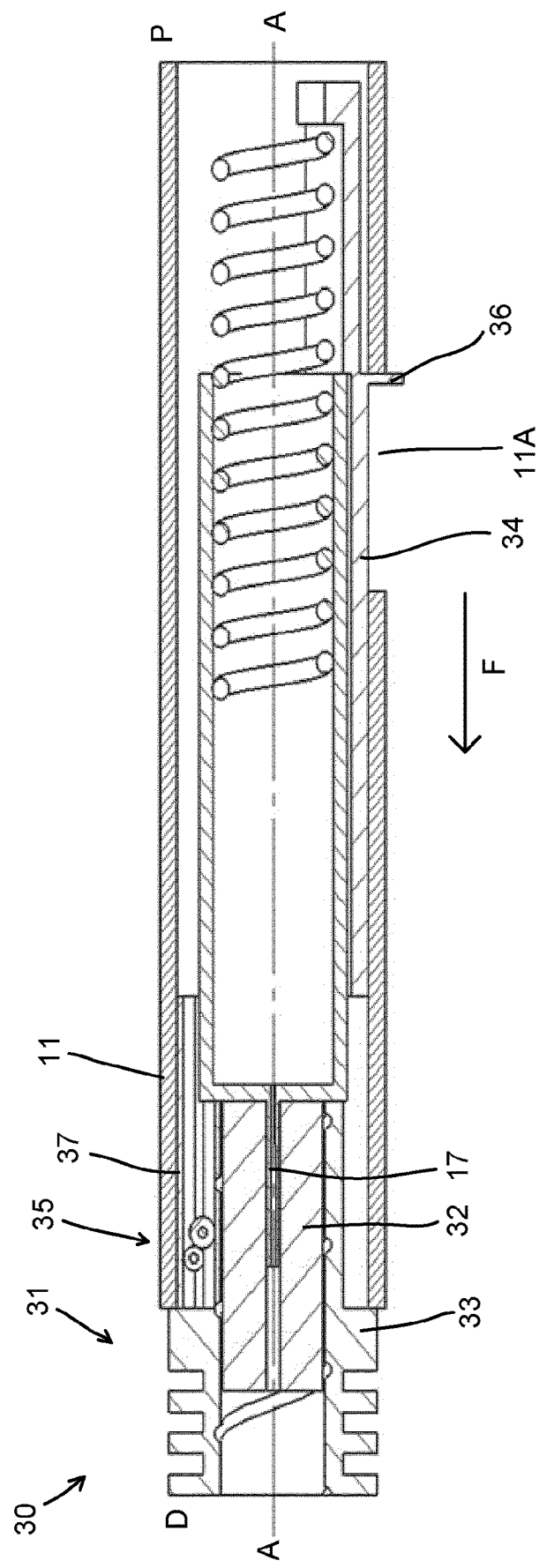
FIG. 4 is a schematic cross-sectional side view of an auto-injector according to a second embodiment, wherein a cap is attached to a body of the auto-injector.
Figure 5:
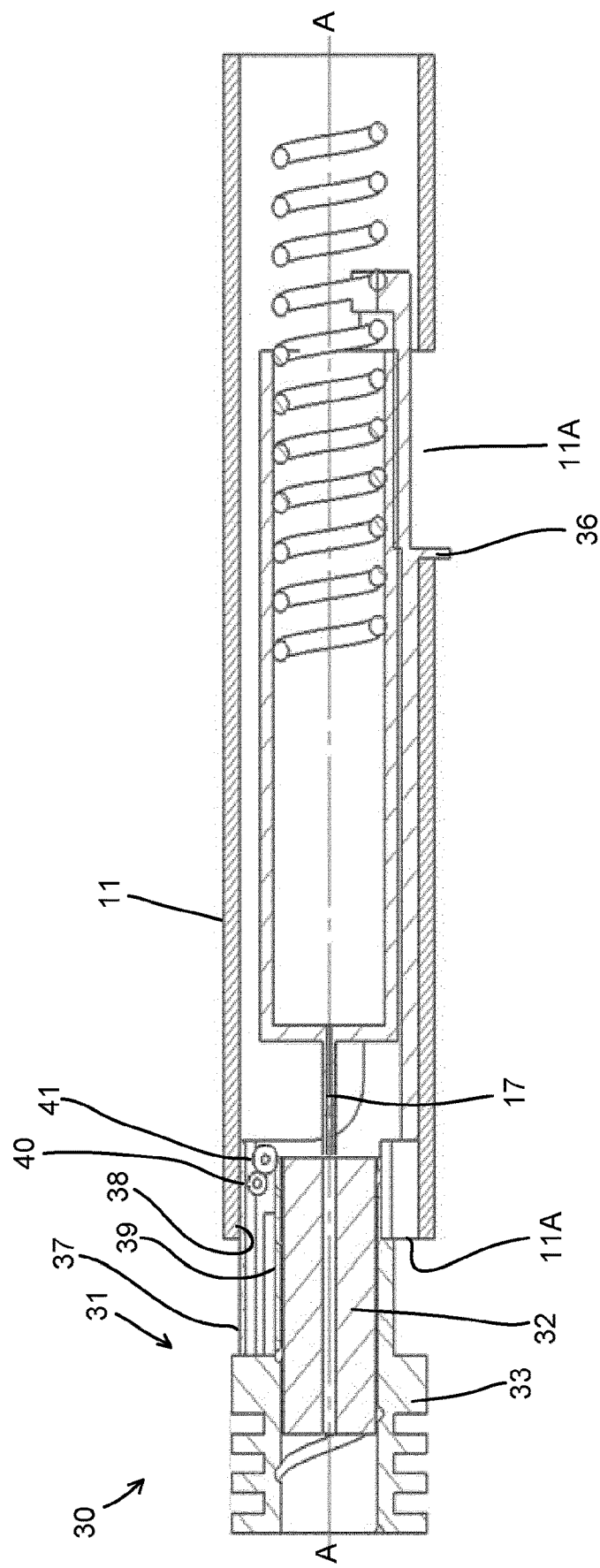
FIG. 5 is a schematic cross-sectional side view of the auto-injector of FIG. 4, wherein the cap is partially removed from the body.

Referring now to FIGS. 4 and 5, an injection device 30 according to a second embodiment is shown. The injection device 30 is in the form of an auto-injector 30 that has similar features to the auto-injector 10 described above in relation to FIGS. 1A and 1B, with like features retaining the same reference numerals. A difference is that the cap 12 of the auto-injector 10 described above is omitted and is replaced with an alternative cap 31.

The cap 31 of the auto-injector 30 of the second embodiment comprises a needle shield 32 and an outer cap 33. The needle shield 32 is received within the outer cap 33. The needle shield 32 is configured to receive the needle 17 such that the needle 17 is shielded.

The cap 31 further comprises an actuator 34 and a gear assembly 35.

The actuator 34 is received in the body 11 of the auto-injector 30 and is slidable relative to the body 11 in the direction of the central axis A-A of the auto-injector 30. The body 11 comprises an aperture 11A in the peripheral wall of the body 11. The actuator 34 comprises a projection 36 that extends out of the aperture 11A in the body 11. The actuator 34 further comprises a longitudinal member 37 that extends out of the open distal end 11A of the body 11 when the projection 36 is slid towards said open distal end 11A.

The gear assembly 35 comprises first and second linear gears 38, 39 and first and second rotary gears 40, 41. The first and second linear gears 38, 39 are in the form of first and second rack gears 38, 39 respectively. The first and second rotary gears 40, 41 are in the form of first and second pinion gears 40, 41 respectively.

The first rack gear 38 is in the form of a plurality of teeth formed in a surface of the longitudinal member 37 such that the first rack gear 38 is fixed relative to the actuator 34. The second rack gear 39 is in the form of a plurality of teeth formed in a peripheral surface of the outer cap 33 such that the second rack gear 39 is fixed relative to the outer cap 33.

The first pinion gear 40 is rotatably mounted to the body 11 such that the teeth of the first pinion gear 40 engage with the teeth of the first rack gear 38. The second pinion gear 41 is rotatably mounted to the body 11 such that the teeth of the second pinion gear 41 engage with the teeth of the first pinion gear 40 and the teeth of the second rack gear 39. Therefore, the first rack gear 38 is coupled to the second rack gear 39 via the first and second pinion gears 40, 41.

The gear assembly 35 is configured such that linear movement of the first rack gear 38 relative to the body 11 in the direction of the central axis A-A of the auto-injector 30 results in rotation of the first pinion gear 40. The rotation of the first pinion gear 40 causes the second pinion gear 41 to rotate, which urges the second rack gear 39 to move linearly in the same direction as the first rack gear 38. Therefore, linear movement of the projection 36 of the actuator 34 relative to the body 11 causes linear movement of the outer cap 33 relative to the body 11 in the same direction.

When the actuator 34 is in a first position (shown in FIG. 4), the projection 36 is located near to the proximal end P of the auto-injector 30 such that the longitudinal member 37 of the actuator 34 is retracted into the body 11.

The cap 31 is initially attached to the body 11 such that the needle 17 is completely received in the needle shield 32 (as shown in FIG. 4) and the actuator 34 is in the first position. Thus, the needle 17 is covered by the needle shield 32 to keep the needle 17 sterile and to prevent the needle 17 from causing injury to the patient.

To inject medicament, the cap 31 is first removed from the body 11. Removal of the cap 31 from the body 11 is achieved by the patient exerting a force on the projection 36 of the actuator 34 to urge the projection 36 relative to the body 11 towards the distal end D of the auto-injector 30 (in the direction of arrow 'F' in FIG. 4). This causes the longitudinal member 37 to be urged out of the open distal end 11A of the body 11 such that the first rack gear 38 is moves linearly relative to the body 11 in the same direction as the projection 36. The linear movement of the first rack gear 38 causes the first pinion gear 40 to rotate, which in turn rotates the second pinion gear 41. The rotation of the second pinion gear 41 causes the second rack gear 39 to move linearly in the same direction as the first rack gear 38 (in the direction of arrow 'F'). The outer cap 33, which is fixed relative to the second rack gear 39, and the needle shield 32, which is fixed relative to the outer cap 33, are therefore urged away from the body 11 such that the needle shield 32 moves away from the needle 17.

The patient continues to exert a force on the projection 36 until the actuator 34 reaches a second position (as shown in FIG. 5), wherein the projection 36 is located closer to the distal end D of the auto-injector 30 than in the first position and the needle shield 32 is separated from the needle 17. The friction between the cap 31 and the body 11 and needle 17 is reduced when the needle shield 32 is separated from the needle 17 such that the cap 31 can easily be removed from the body 11 simply by pulling the outer cap 33 away from the body 11. Optionally, the cap 31 may be retained on the body 11 by a clip (not shown). Thus, after the needle shield 32 is separated from the needle 17, the user is able to unclip the cap 31 from the body 11 to remove the cap 31 from the body 11.

With the cap 31 removed from the body 11, the longitudinal member 37 is pressed up against an injection site of the patient. The dispense button 13 is then pressed to cause the dispense mechanism (not shown) to move the needle 17 towards the injection site and to dispense medicament to the injection site. In an alternative embodiment (not shown), the dispense mechanism is configured such that the movement of the needle towards the injection site and/or the dispensing of the medicament occurs automatically when the longitudinal member is pressed against the injection site.

The gear assembly 35 is configured to reduce the force that must be exerted by the patient to remove the needle shield 32 from the needle 17. More specifically, the gear assembly 35 is configured to have a reduced gear ratio such that a first force exerted on the first rack gear 38 by the patient, via the actuator 34, results in a second force, which is larger than the first force, being exerted on needle shield 32 by the second rack gear 39. Consequently, movement of the actuator 34 relative to the body 11 by a first distance results in movement of the outer cap 33 relative to the body 11 by a second distance that is smaller than the first distance. This reduced gear ratio may be achieved by making the first pinion gear 40 smaller in diameter than the second pinion gear 41. The gear assembly 35 therefore makes removal of the cap 31 from the body 11 easier because the force exerted on the projection 36 of the actuator 35 by the patient is translated into a greater force acting on the needle shield 32 to urge the needle shield 32 away from the needle 17. In addition, the actuator 34 and gear assembly 35 arrangement allows for a smooth and controlled separation of the needle shield 32 from the needle 17.

The actuator 34 may comprise a visual indicator that is visible through the aperture 11A in the body 11 when the actuator 34 is in the first position to indicate to the patient that the needle shield 32 is attached to the needle 17 and must be removed prior to injection.

In the above described embodiment, the longitudinal member 37 extends out of the open distal end 11A of the body 11 when the projection 36 is slid towards the open distal end 11A. Thus, the longitudinal member 37 is pressed against the injection site of the patient. However, in an alternative embodiment (not shown), the longitudinal member is urged towards the open distal end of the body when the projection is slid towards said open distal end of the body but does not extend out of said open distal end. In such an alternative embodiment, the open distal end of the body is pressed against the injection site prior to the medicament being dispensed.

In the above described embodiments, the needle is moved relative to the body by a dispensing mechanism such that the needle is moved towards the injection site. However, in alternative embodiments (not shown) the needle remains stationary relative to the body. In one alternative embodiment (not shown), the longitudinal member is retractable into the open distal end of the body when the needle shield has been removed and the longitudinal member is pressed against the injection site such that the needle projects from the open distal end of the body and penetrates the injection site. Optionally, the movement of the longitudinal member into the body when the longitudinal member is pressed against the injection site may be decoupled from the projection such that movement of the longitudinal member into the body does not cause a corresponding movement of the projection. This may be achieved by making the rack and linear gears a ratchet arrangement such that they only engage in one direction of movement.

In the above described embodiment the needle shield 32 is separated from the needle 17 but the cap 31 is still retained on the body 11 when the actuator 34 is moved from the first position to the second position. The cap 31 is then removed from the body 11 by the user. However, in an alternative embodiment (not shown), the actuator is configured such that the cap is completely removed from the body when the actuator is moved from the first position to the second position. In one such embodiment, the needle shield is fixedly secured to the outer cap such that when the needle shield is urged away from the body by the longitudinal member the outer cap is also urged away from the body.

Although in the above described embodiment the auto-injector 30 comprises one gear assembly 35, in alternative embodiments (not shown) the auto-injector comprises a plurality of gear assemblies. In one such alternative embodiment, the auto-injector comprises three gear assemblies. Each of the gear assemblies comprises first and second rack gears and first and second pinion gears. The gear assemblies are arranged about the central axis of the auto-injector. Embodiments having a plurality of gear assemblies have been found to be advantageous when the first and second linear gears and the first and second rotary gears are friction gears, since the corresponding gears of at least one of the gear assemblies are always urged against each other such that the friction between the gears is increased.

Although in the above described first and second embodiments the linear gears 28, 38, 39 and rotary gears 29, 40, 41 have teeth, in alternative embodiments (not shown), the gears do not comprise teeth. In one such alternative embodiment, the linear gears 28, 38, 39 and the rotary gears 29, 40, 41 are friction gears, engaging via friction rather than having teeth that mesh.

Figure 6:
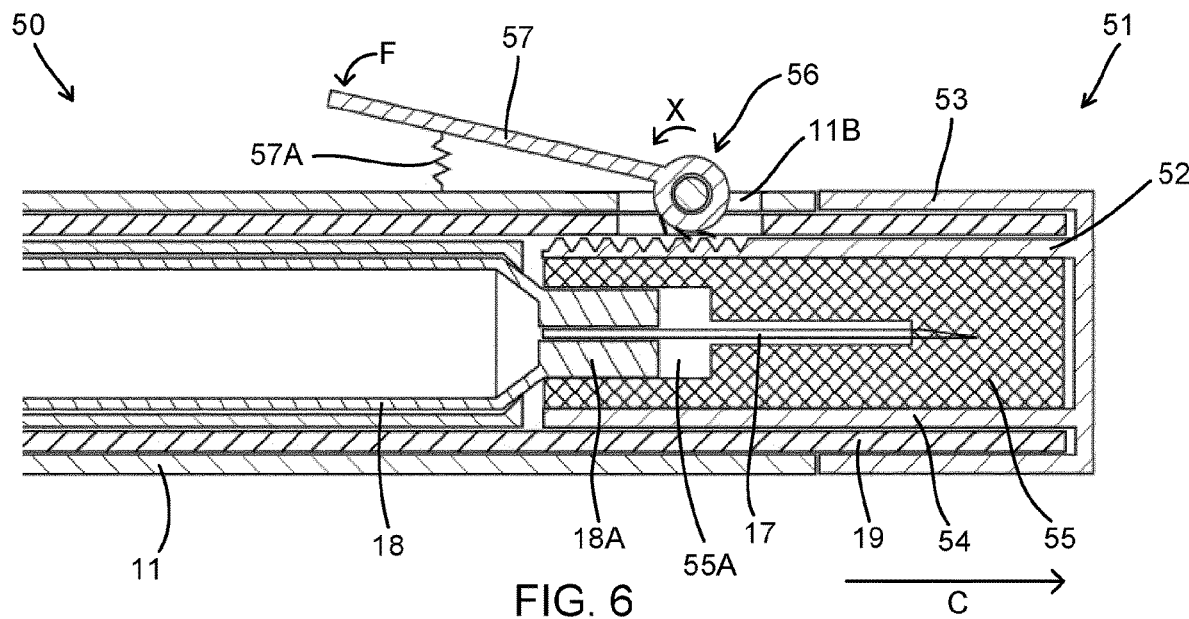
FIG. 6 is a schematic cross-sectional side view of a part of an auto-injector according to a third embodiment, wherein a cap is attached to a body of the auto-injector; and, FIG. 7 is a schematic cross-sectional side view of said part of the auto-injector of FIG. 6, wherein the cap is partially removed from the body.
Figure 7:
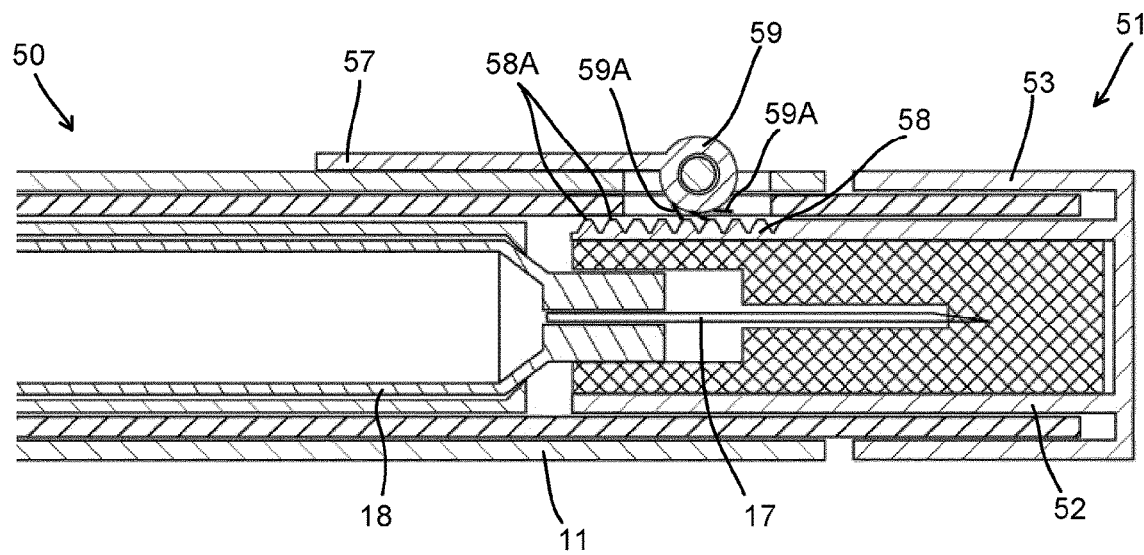

Referring now to FIGS. 6 and 7, an injection device 50 according to a third embodiment is shown. The injection device 50 is in the form of an auto-injector 50 that has similar features to the auto-injector 20 of the first embodiment described above in relation to FIGS. 2 and 3, with like features retaining the same reference numerals. A difference is that the cap 21 of the auto-injector 20 described above is omitted and is replaced with an alternative cap 51.

The cap 51 of the auto-injector 50 of the third embodiment comprises a needle shield 52 and an outer cap 53. The needles shield 52 is located within the outer cap 53 and is fixed therewith.

The needle shield 52 comprises a housing 54 and an inner sheath 55. The inner sheath 55 is fixedly secured in the housing 54. The inner sheath 55 comprises a cylindrical recess 55A. The recess 55A is configured to receive the end portion 18A of the syringe 18 such that the needle 17 is shielded by the inner sheath 55. The friction between the inner sheath 55 and the end portion 18A of the syringe 18 is sufficient to hold the needle shield 52 in place covering the needle 17.

The cap 51 further comprises a gear assembly 56 and an actuator 57. The gear assembly 56 comprises a linear gear 58, in the form of a rack gear 58, and a rotary gear 59, in the form of a ratchet gear 59. The rack gear 58 is in the form of a plurality of teeth 58A formed in a peripheral surface of the housing 54 of the needle shield 52 such that the rack gear 58 is fixed relative to the inner sheath 55.

The ratchet gear 59 is rotatably mounted in an aperture 11B in the peripheral wall of the body 11. The ratchet gear 59 also extends through an aperture in a needle sleeve 19 that is located inside the body 11. The ratchet gear 59 comprises a plurality of flexible elements 59A that extend away from the rotational axis of the ratchet gear 59. The ratchet gear 59 is arranged such that the flexible elements 59A of the ratchet gear 59 engage with the teeth 58A of the rack gear 58.

The gear assembly 56 is configured such that rotation of the ratchet gear 59 in a first rotational direction (shown by arrow 'X' in FIG. 6) causes the flexible elements 59A to be urged against the teeth 58A of the rack gear 58 such that the rack gear 58 is moved linearly away from the body 11 (in the direction of arrow 'C' in FIG. 6). Moreover, the gear assembly 56 is configured such that rotation of the ratchet gear 59 in a second rotational direction, opposite the first rotational direction X, causes the flexible elements 59A of the ratchet gear 59 to flex and move over the surface of the teeth 58A of the rack gear 58 such that the ratchet gear 59 rotates without linear movement of the rack gear 58. Thus, the ratchet gear 59 is configured to drive the rack gear 58 in only one direction.

The actuator 57 is in the form of a lever arm 57. The lever arm 57 is fixed at one end to the ratchet gear 59 such that the patient can exert a force on the lever arm 57 to pivot the lever arm 57 about the rotational axis of the ratchet gear 59 such that the ratchet gear 59 is urged to rotate. As discussed, rotation of the ratchet gear 59 in the first rotational direction X causes the rack gear 58 to move linearly relative to the ratchet gear 59 in the direction of the central axis of the auto-injector 50 such that the needle shield 52 is moved away from the body 11.

When the lever arm 57 is in a first position (shown in FIG. 6), the lever arm 57 extends away from the body 11 such that the free end of the lever arm 57 is spaced from the body 11. A biasing member 57A, for example a spring or portion of resilient material, biases the lever arm 57 into the first position. Furthermore, when the lever arm 57 is in the first position the needle shield 52 is received in a needle sleeve 19, which extends out of the open distal end of the body 11.

The cap 51 is initially attached to the body 11 such that the end portion 18A of the syringe 18 is completely received in the recess 55A of the inner sheath 55 (as shown in FIG. 6) and the lever arm 57 is in the first position. Thus, the needle 17 is covered by the needle shield 52 to keep the needle 17 sterile and to prevent the needle 17 from causing injury to the patient.

To inject medicament, the cap 51 is first removed from the body 11. Removal of the cap 51 from the body 11 is achieved by the patient exerting a force on the lever arm 51 relative to the body 11 (in the direction of arrow 'F' in FIG. 6) to urge the lever arm 57 to pivot about the rotational axis of the ratchet gear 59 such that the free end of the lever arm 57 moves towards the body 11. This causes the ratchet gear 59 to be urged to rotate in the first rotational direction X such that the flexible elements 59A of the ratchet gear 59 are urged against the teeth 58A of the rack gear 58. Therefore, the rack gear 58 is urged to move linearly relative to the body 11 (in the direction of arrow 'C' in FIG. 6) such that the needle shield 52 is urged axially away from the body 11.

The needle 17 is fixed relative to the body 11. Therefore, as the needle shield 52 is urged away from the body 11 due to the patient moving the lever arm 57 away from the first position, the needle shield 52 and outer cap 53 moves axially away from the needle 17 such that the inner sheath 55 is removed from the end portion 18A of the syringe 18. The patient continues to move the lever arm 57 away from the first position until it is rotated about the rotational axis of the ratchet gear 59 to a second position (shown in FIG. 7) wherein the free end of the lever arm 57 abuts the body 11 and the lever arm 57 extends substantially parallel to the central axis of the auto-injector 50. The lever arm 57 is then released such that the biasing member 57A moves the lever arm 57 back to the first position. The user then urges the lever arm 57 into the first position again such that the ratchet gear 59 rotates in the first rotational direction X and thus the cap 51 is urged further away from the body 11 and syringe 18. This reciprocal movement of the lever arm 57 relative to the body 11 is repeated until the end portion 18A of the syringe 18 is no longer received in the recess 55A of the inner sheath 55 such that the friction between the cap 51 and the body 11 and/or needle sleeve 19 is reduced and so the cap 51 can easily be removed from the body 11 simply by pulling the outer cap 53 away from the body 11.

With the cap 51 removed from the body 11, the open distal end 19A of the needle sleeve 19 is pressed up against an injection site of the patient. The dispense button (not shown) is then pressed to cause the dispense mechanism (not shown) to move the needle 17 towards the injection site and to dispense medicament to the injection site. In an alternative embodiment (not shown), the needle sleeve is omitted and instead the open distal end of the body is pressed up against the injection site of the patient.

The reciprocal movement of the lever arm 57 relative to the body 11 may be easier for a user to perform, since only a small range of movement of the lever arm 57 relative to the body 11 is required to urge the needle shield 52 and outer cap 53 away from the body 11. In addition, the gear assembly 56 may be such that the force exerted on the lever arm 57 by the user is translated into a larger force acting on the needle shield 52, thereby facilitating removal of the cap 51 from the body 11.

In an alternative to the above described embodiment, the biasing member 57A is omitted and instead the user manually moves the lever arm 57 from the second position to the first position.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance, which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor-binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:
1. An injection device comprising:
a body for holding a syringe that has a needle at one end;
a cap that is removably attached to the body, wherein the cap has a needle shield to cover the needle, wherein the needle shield is completely detachable from the body to expose the needle;
a gear assembly comprising a first rotary gear and a first linear gear to engage with the first rotary gear, wherein the first linear gear is fixed relative to the needle shield, the gear assembly being configured such that rotation of the first rotary gear drives the first linear gear to urge the needle shield away from the body; and, an actuator configured to rotate the first rotary gear.

2. The injection device according to claim 1, wherein the first linear gear is formed in a peripheral surface of the needle shield.

3. The injection device according to claim 1, comprising an outer cap, wherein the needle shield is slidable relative to the outer cap such that the needle shield slides relative to the outer cap when the first rotary gear is rotated.

4. The injection device according to claim 1, wherein the first rotary gear is rotatably coupled to the body.

5. The injection device according to claim 1, wherein the first rotary gear is rotatably coupled to the cap.

6. The injection device according to claim 1, wherein the actuator comprises a lever arm that has an end fixed relative to the first rotary gear.

7. The injection device according to claim 1, wherein the actuator is slidable relative to the body to rotate the first rotary gear.

8. The injection device according to claim 7, wherein the actuator comprises a second linear gear that is configured to cause the first rotary gear to rotate when the actuator is slid relative to the body.

9. The injection device according to claim 8, comprising a second rotary gear that couples the second linear gear to the first rotary gear.

10. The injection device according to claim 1, wherein the gear assembly is configured to have a gear ratio such that a force exerted on the actuator translates into a larger force being exerted on the needle shield.

11. The injection device according to claim 1, comprising a plurality of gear assemblies.

12. The injection device according to claim 1, comprising the syringe having the needle at one end, the syringe being received in the body, wherein the needle shield is in frictional engagement with the syringe when the cap is attached to the body.

13. The injection device according to claim 12, wherein the syringe contains a medicament.

14. The injection device according to claim 1, wherein the injection device is an auto-injector.

15. The injection device of claim 1, wherein the needle shield has a closed end that is configured to cover the needle.

16. A method of removing a cap from a body of an injection device, wherein the body holds a syringe that has a needle at one end and the cap is removably attached to the body and has a needle shield to cover the needle, wherein the first linear gear is fixed relative to the needle shield; wherein the needle shield is completely detachable from the body to expose the needle, the method comprising:

moving an actuator relative to the cap or body to rotate a first rotary gear, wherein the rotation of the first rotary gear drives a first linear gear, coupled to the first rotary gear, to urge the needle shield away from the body.

17. The method of claim 16, wherein the actuator comprises a second linear gear, and the method further comprises moving the actuator relative to the body such that the second linear gear causes the first rotary gear to rotate.

18. The method of claim 16, wherein a first rotary gear is coupled to the body of the syringe.

19. The method of claim 16, wherein the needle shield is in frictional engagement with the syringe when the cap is attached to the body.

20. The method of claim 16, wherein a force exerted on the actuator translates into a larger force being exerted on the needle shield.

21. The method of claim 20, wherein the force exerted on the actuator translates into a larger force on the needle shield due to a gear ratio between the first rotary gear and the first linear gear.

* * * * *